(12) United States Patent
Reynolds et al.

(10) Patent No.: US 7,517,825 B2
(45) Date of Patent: Apr. 14, 2009

(54) AROMATIC TRANSALKYLATION USING A LZ-210 ZEOLITE

(75) Inventors: Thomas M. Reynolds, Mobile, AL (US); Christopher J. Garrett, Mobile, AL (US); Deng-Yang Jan, Elk Grove Village, IL (US); Robert J. Schmidt, Barrington, IL (US); Mathias P. Koljack, Gilberts, IL (US)

(73) Assignee: UOP LLC, Des Planies, IL (US)

( * ) Notice: Subject to any disclaimer, the term of this patent is extended or adjusted under 35 U.S.C. 154(b) by 0 days.

(21) Appl. No.: 11/622,925

(22) Filed: Jan. 12, 2007

(65) Prior Publication Data

US 2008/0171901 A1 Jul. 17, 2008

(51) Int. Cl.
*B01J 29/06* (2006.01)

(52) U.S. Cl. ............................. 502/60; 502/64; 502/79

(58) Field of Classification Search ............... 502/63.64, 502/79
See application file for complete search history.

(56) References Cited

U.S. PATENT DOCUMENTS

| | | | |
|---|---|---|---|
| 3,130,007 A | 4/1964 | Breck | |
| 3,442,795 A | 5/1969 | Kerr | |
| 3,887,630 A | 6/1975 | Ward | |
| 3,929,672 A | 12/1975 | Ward | |
| 4,503,023 A | 3/1985 | Breck et al. | |
| 4,597,956 A | 7/1986 | Hinchey et al. | |
| 4,735,928 A | 4/1988 | Best et al. | |
| 4,774,377 A | 9/1988 | Barger et al. | |
| 4,861,935 A | 8/1989 | Bakas et al. | |
| 4,954,325 A | 9/1990 | Rubin et al. | |
| 5,013,699 A | 5/1991 | Vassilakis et al. | |
| 5,030,786 A | 7/1991 | Shamshoum et al. | |
| 5,030,787 A | 7/1991 | Absil et al. | |
| 5,036,033 A | 7/1991 | West et al. | |
| 5,073,653 A | 12/1991 | Butler | |
| 5,157,180 A | 10/1992 | West et al. | |
| 5,160,033 A | 11/1992 | Vassilakis et al. | |
| 5,177,285 A | 1/1993 | Van Opdorp et al. | |
| 5,207,892 A | 5/1993 | Vassilakis et al. | |
| 5,208,197 A | 5/1993 | Vassilakis et al. | |
| 5,236,575 A | 8/1993 | Bennett et al. | |
| 5,240,889 A | 8/1993 | West et al. | |
| 5,275,720 A | 1/1994 | Ward | |
| 5,324,877 A | 6/1994 | West et al. | |
| 5,362,697 A | 11/1994 | Fung et al. | |
| 5,446,223 A | 8/1995 | Smith, Jr. | |
| 5,536,687 A * | 7/1996 | Ward ........................ | 502/67 |
| 5,690,810 A | 11/1997 | Lawrence et al. | |
| 5,827,491 A | 10/1998 | Emerson et al. | |
| 5,998,684 A | 12/1999 | Ho et al. | |
| 6,150,578 A | 11/2000 | Ho et al. | |
| 6,500,998 B1 | 12/2002 | Jan et al. | |
| 6,506,935 B1 | 1/2003 | Kulprathipanja et al. | |
| 6,642,168 B1 | 11/2003 | Latus | |

FOREIGN PATENT DOCUMENTS

| | | |
|---|---|---|
| EP | 0 247 679 A2 | 12/1987 |
| EP | 485683 | 5/1992 |
| EP | 467007 B1 | 10/1992 |
| WO | WO 2006/107452 A1 | 10/2006 |
| WO | WO 2006/107462 A1 | 10/2006 |
| WO | WO 2006/107470 A1 | 10/2006 |
| WO | WO 2006/107471 A1 | 10/2006 |

OTHER PUBLICATIONS

Doelle, et al., "Sorption and Catalytic Reaction in Pentasil Zeolites. Influence of Preparation . . . Kinetics", Journal of Catalysis 71, 27-40 (1981), no month.

Cundy, et al., "The Hydrothermal Synthesis of Zeolites: History and Development . . . Time", Chem Rev. 2003, 103, 683-701, no month.

Lawton, et al., "Zeolite MCM-49: A Three Dimentional MCM-22 . . . Crystallization", J Phys. Chem 1996, 100, 3788-3798, no month.

\* cited by examiner

*Primary Examiner*—Elizabeth D Wood
(74) *Attorney, Agent, or Firm*—David J Piasecki (57) ABSTRACT

A process for converting polyalkylaromatics to monoalkylaromatics, particularly cumene, in the presence of a modified LZ-210 zeolite is disclosed. The process attains greater selectivity, reduced formation of undesired byproducts, and increased activity.

22 Claims, 4 Drawing Sheets

AROMATIC TRANSALKYLATION USING A LZ-210 ZEOLITE

TECHNICAL FIELD

The process disclosed herein relates to the production of monoalkylaromatics, in particular cumene, from polyalkylaromatics, in particular polyisopropylbenzenes (PIPBs) including, but not necessarily limited to, triisopropylbenzene (TIPB) and diisopropylbenzene (DIPB). The process relates to the use of a modified LZ-210 zeotite derived from a Y zeolite as a catalyst in the transalkylation of such polyalkylaromatics.

BACKGROUND

The following description will make specific reference to the use of the catalyst disclosed herein in the transalkylation of PIPBs with benzene to afford cumene, but it is to be recognized that this is done solely for the purpose of clarity and simplicity of exposition. Frequent reference will be made herein to the broader scope of this application for emphasis.

Cumene is a major article of commerce, with one of its principal uses being a source of phenol and acetone via its air oxidation and a subsequent acid-catalyzed decomposition of the intermediate hydroperoxide.

Because of the importance of both phenol and acetone as commodity chemicals, there has been much emphasis on the preparation of cumene and the literature is replete with processes for its manufacture. The most common and perhaps the most direct method of preparing cumene is the alkylation of benzene with propylene, especially using an acid catalyst.

Another common method of preparing cumene is the transalkylation of benzene with PIPB, particularly di-isopropylbenzene (DIPB) and tri-isopropylbenzene (TIPB), especially using an acid catalyst. Any commercially feasible transalkylation process must satisfy the requirements of a high conversion of polyalkylated aromatics and a high selectivity to monoalkylated products.

The predominant orientation of the reaction of benzene with PIPB resulting in cumene corresponds to Markownikoff addition of the propyl group. However, a small but very significant amount of the reaction occurs via anti-Markownikoff addition to afford n-propylbenzene (NPB). The significance of NPB formation is that it interferes with the oxidation of cumene to phenol and acetone, and consequently cumene used for oxidation must be quite pure with respect to NPB content.

Because cumene and NPB are difficult to separate by conventional means (e.g. distillation), the production of cumene via the transalkylation of benzene with PIPB must be carried out with a minimal amount of NPB production. One important factor to take into consideration is that the use of an acid catalyst for the transalkylation results in increased NPB formation with increasing temperature. Thus, to minimize NPB formation, the transalkylation should be carried out at as low a temperature as possible.

Since DIPB and TIPB are not only the common feeds for the transalkylation of benzene with PIPBs but also the common byproducts of the alkylation of benzene with propylene when forming cumene, transalkylation is commonly practiced in combination with alkylation to minimize the production of less valuable byproducts and to produce additional cumene. In such a combination process, the cumene produced by both alkylation and transalkylation is typically recovered in a single product stream. Since NPB is also formed in alkylation and the amount of NPB formation in alkylation increases with increasing temperature, the NPB production in both alkylation and transalkylation must be managed relative to one another so that the cumene product stream is relatively free of NPB.

What is needed is an optimum transalkylation catalyst for, e.g., cumene production, with sufficient activity to effect transalkylation at acceptable reaction rates at temperatures sufficiently low to avoid unacceptable NPB formation. Because Y zeolites show substantially greater activity than many other zeolites, they have received close scrutiny as a catalyst in aromatic transalkylation. However, a problem exists in that Y zeolites effect transalkylation at unacceptably low rates at the low temperatures desired to minimize NPB formation.

Therefore, in order for a commercial process based on Y zeolites to become a reality, it is necessary to increase catalyst activity—i.e., increase the rate of cumene production at a given, lower temperature.

BRIEF SUMMARY OF THE DISCLOSURE

Processes disclosed herein use a catalyst made by making modifications to native Y zeolite so that the catalyst shows decreased NPB formation and increased activity relative to other Y zeolites.

Accordingly, in an embodiment, a transalkylatable aromatic and an aromatic are contacted with a catalyst comprising a modified Y zeolite and having less than about 0.2 wt % of a metal hydrogenation component.

In such embodiment, the modified Y zeolite is prepared be treating a starting material, such as a Y-54 zeolite, with aqueous fluorosilicate solution resulting in a LZ-210 zeolite having a first unit cell size. Thereafter, the fluorosilicate-treated samples are subjected to steaming at temperatures ranging from about 550° C. (1022° F.) to about 850° C. (1562° F.) to produce a steamed LZ-210 zeolite containing sodium cations, having a first bulk $Si/Al_2$ molar ratio, and having a second unit cell size less than the first unit cell size. Finally, the steamed LZ-210 zeolite is contacted with a sufficient amount of an aqueous solution of ammonium ions and having a pH of less than about 4 for a sufficient time to exchange at least some of the sodium cations in the steamed LZ-210 zeolite for ammonium ions and to produce the modified LZ-210 zeolite having a second bulk $Si/Al_2$ molar ratio greater than the first bulk $Si/Al_2$ molar ratio and in the range of from about 6.5 to about 27. The unit cell size of the modified Y zeolite is in the range of from about 24.34 to about 24.58 Å. Then, an acid extraction can be performed to remove the extra-framework aluminum.

Before the Y zeolite is treated with fluorosilicate salt or after, or both, the catalyst may be subject to an ammonium ion exchange(s) to reduce the sodium content of the catalyst to a $Na_2O$ wt % of 1 wt % or lower while maintaining the first bulk $Si/Al_2$ molar ratio.

In another embodiment, fluorosilicate treated Y zeolite (or LZ-210 zeolite) can be ammonium exchanged, without going through the steaming step, to lower $Na_2O$ contents further to produce a material suitable for this disclosure.

The disclosed treatment affects the number and nature of extra-framework aluminum (and Lewis acid sites), as shown by a changed $Si/Al_2$ ratio and a changed unit cell size thereby improving diffusion characteristics, increasing catalyst activity, and lowering the NPB formation.

It has been surprisingly found that treating the Y zeolite with (1) a fluorosilicate solution, followed by (2) steaming, and then by (3) treating with aqueous ammonium ion solution having a low pH to increase the bulk Si/Al$_2$ ratio, affords a superior LZ-210 zeolite for the transalkylation of PIPBs to cumene and PEBs to EB Other embodiments of the process disclosed herein are described in the detailed description.

DETAILED DESCRIPTION

The process disclosed herein uses a catalyst that comprises a crystalline zeolitic molecular sieve. The preferred molecular sieves for use in the catalyst disclosed herein are modified Y zeolites. U.S. Pat. No. 3,130,007, which is hereby incorporated herein by reference in its entirety, describes Y-type zeolites. The modified Y zeolites suitable for use in preparing the catalyst disclosed herein are generally derived from Y zeolites by treatment which results in a significant modification of the Y zeolite framework structure and composition, usually an increase in the bulk Si/Al$_2$ mole ratio to a value typically above 6.5 and/or a reduction in the unit cell size. It will be understood, however, that, in converting a Y zeolite starting material to a modified Y zeolite useful in the process disclosed herein, the resulting modified Y zeolite may not have exactly the same X-ray powder diffraction pattern for Y zeolites as described in the '007 patent. The modified Y zeolite may have an X-ray powder diffraction pattern similar to that of the '007 patent but with the d-spacings shifted somewhat due, as those skilled in the art will realize, to cation exchanges, calcinations, etc., which are generally necessary to convert the Y zeolite into a catalytically active and stable form.

The modified Y zeolite useful in the process disclosed herein has a unit cell size of from about 24.34 to about 24.58 Å, preferably from about 24.36 to about 24.55 Å. The modified Y zeolite has a bulk Si/Al$_2$ molar ratio of from about 6.5 to about 27, more preferably from about 6.5 to about 23.

In preparing the modified Y zeolite component of the catalysts used in the process described herein, the starting material may be a Y zeolite in alkali metal (e.g., sodium) form such as described in the '007 patent. The alkali metal form Y zeolite is ion-exchanged with ammonium ions, or ammonium ion precursors such as quaternary ammonium or other nitrogen-containing organic cations, to reduce the alkali metal content to less than about 4 wt %, preferably less than about 3 wt %, more preferably less than about 2.5 wt %, expressed as the alkali metal oxide (e.g., Na$_2$O) on a dry basis. As used herein, the weight of the zeolite on a water-free or dry basis means the weight of the zeolite after maintaining the zeolite at a temperature of about 900° C. (1652° F.) for roughly 2 hours.

Optionally, the starting zeolite can also contain or at some stage of the modification procedure be ion-exchanged to contain rare earth cations to the degree that the rare earth content as RE$_2$O$_3$ constitutes from about 0.1 to about 12.5 wt % of the zeolite (anhydrous basis), preferably from about 8.5 to about 12 wt %. It will be understood by those skilled in the art that the ion-exchange capacity of the zeolite for introducing rare earth cations decreases during the course of the disclosed treatment process. Accordingly, if rare earth cation exchange is carried out, for example, as the final step of the preparative process, it may not be possible to introduce even the preferred amount of rare earth cations. The framework Si/Al$_2$ ratio of the starting Y zeolite can be within the range of less than about three 3 to about 6, but is advantageously greater than about 4.8.

Y zeolites which which may be used in the process disclosed herein may be prepared by dealuminating a Y zeolite having an overall silica to alumina mole ratio below about 5 and are described in detail in U.S. Pat. Nos. 4,503,023, 4,597, 956, 4,735,928 and 5,275,720 which are hereby incorporated herein by reference. The '023 patent discloses another procedure for dealuminating a Y zeolite involving contacting the Y zeolite with an aqueous solution of a fluorosilicate salt using controlled proportions, temperatures, and pH conditions which avoid aluminum extraction without silicon substitution. The '023 patent discloses that the fluorosilicate salt is used as the aluminum extractant and also as the source of extraneous silicon which is inserted into the Y zeolite structure in place of the extracted aluminum. The salts have the general formula:

$$(A)_{2/b}SiF_6$$

wherein A is a metallic or nonmetallic cation other than H$^+$ having the valence "b." Cations represented by "A" are alkylammonium, NH$_4^+$, Mg$^{++}$, Li$^+$, Na$^+$, K$^+$, Ba$^{++}$, Cd$^{++}$, Cu$^{++}$, H$^+$, Ca$^{++}$, Cs$^+$, Fe$^{++}$, Co$^{++}$, Pb$^{++}$, Mn$^{++}$, Rb$^+$, Ag$^+$, Sr$^{++}$, Ti$^+$, and Zn$^{++}$.

A preferred member of this group of Y zeolites is known as LZ-210, a zeolitic aluminosilicate molecular sieve described in the '023 patent LZ-210 zeolites and the other zeolites of this group are conveniently prepared from a Y zeolite starting material In one embodiment, the LZ-210 zeolite has an overall silica to alumina mole ratio from about 5.0 to about 11.0. The unit cell size ranges from about 24.38 to about 24.50 angstrom, preferably from about 24.40 to about 24.44 angstrom. The LZ-210 class of zeolites used in the process and composition disclosed herein have a composition expressed in terms of mole ratios of oxides as in the following formula:

$$(0.85-1.1)M_{2/n}O:Al_2O_3:xSiO_2$$

wherein "M" is a cation having the valence "n" and "x" has a value from 5.0 to 11.0.

In general, LZ-210 zeolites may be prepared by dealuminating Y-type zeolites using an aqueous solution of a fluorosilicate salt, preferably a solution of ammonium hexafluorosilicate. The dealumination can be accomplished by placing a Y zeolite, normally but not necessarily an ammonium exchanged Y zeolite, into an aqueous reaction medium such as an aqueous solution of ammonium acetate, and slowly adding an aqueous solution of ammonium fluorosilicate. After the reaction is allowed to proceed, a zeolite having an increased overall silica to alumina mole ratio is produced. The magnitude of the increase is dependent at least in part on the amount of fluorosilicate solution contacted with the zeolite and on the reaction time allowed. Normally, a reaction time of between about 10 and about 24 hours is sufficient for equilibrium to be achieved. The resulting solid product, which can be separated from the aqueous reaction medium by conventional filtration techniques, is a form of LZ-210 zeolite. In some cases this product may be subjected to a steam calcination by methods well known in the art. For instance, the product may be contacted with water vapor at a partial pressure of at least 1.4 kPa(a) (0.2 psi(a)) for a period of between about ¼ to about 3 hours at a temperature between about 482° C. (~900° F.) and about 816° C. (~1500° F.) in order to provide greater crystalline stability. In some cases the product of the steam calcination may be subjected to an ammonium-exchange by methods well known in the art. For instance, the product may be slurried with water after which an ammonium salt is added to the slurry. The resulting mixture is typically heated for a period of hours, filtered, and washed with water. Methods of steaming and ammonium-exchanging LZ-210 zeolite are described in U.S. Pat. Nos. 4,503,023, 4,735,928, and 5,275,720.

In one embodiment, the ammonium exchange is followed by the treatment with an aqueous solution of a fluorosilicate salt to increase Si/Al$_2$ ratio, enhancing the hydrothermal stability and lowering the propensity to form extra-framework aluminum.

The final low pH, ammonium ion exchange of the LZ-210 zeolite, which is preferred, can be carried out in the same manner as in the case of the initial ammonium exchange of the Y zeolite (and/or LZ-210 zeolite as discussed above) except that the pH of the exchange medium is lowered to below about 4, preferably to below about 3, at least during some portion of the ion-exchange procedure. The lowering of the pH is readily accomplished by the addition of an appropriate mineral or organic acid to the ammonium ion solution. Nitric acid is especially suitable for this purpose. Preferably, acids which form insoluble aluminum salts are avoided. In performing the low pH ammonium ion exchange, both the pH of the exchange medium, the quantity of exchange medium relative to the zeolite and the time of contact of the zeolite with the exchange medium are significant factors. It is found that so long as the exchange medium is at a pH below 4, sodium cations are exchanged for hydrogen cations in the zeolite and, in addition, at least some aluminum, predominately non-framework and some framework, is extracted. The efficiency of the process is improved, however, by acidifying the ion exchange medium using more acid than is required to lower the pH to just below 4. As will be evident from the data set forth below, the more acidic the exchange medium is, the greater the tendency to extract framework as well as non-framework aluminum from the zeolite. The extraction procedure is carried out to a degree sufficient to produce a zeolite product having a bulk Si/Al$_2$ molar ratio ranging from about 6.5 to about 27. In other embodiments, the bulk Si/Al$_2$ molar ratio ranges from about 6.5 to about 23 or more preferably from about 6.5 to about 20.

Although the disclosed catalyst may contain a metal hydrogenation catalytic component, such a component is not a requirement. Based on the weight of the catalyst, such a metal hydrogenation catalytic component may be present at a level of less than 0.2 wt % or less than 0.1 wt % calculated as the respective monoxide of the metal component, or the catalyst may be devoid of any metal hydrogenation catalytic component. If present, the metal hydrogenation catalytic component can exist within the final catalyst composite as a compound such as an oxide, sulfide, halide and the like, or in the elemental metallic state. As used herein, the term "metal hydrogenation catalytic component" is inclusive of these various compound forms of the metals. The catalytically active metal can be contained within the inner adsorption region, i.e., pore system, of the zeolite constituent, on the outer surface of the zeolite crystals or attached to or carried by a binder, diluent or other constituent, if such is employed. The metal can be imparted to the overall composition by any method which will result in the attainment of a highly dispersed state. Among the suitable methods are impregnation, adsorption, cation exchange, and intensive mixing. The metal can be copper, silver, gold, titanium, chromium, molybdenum, tungsten, rhenium, manganese, zinc, vanadium, or any of the elements in IUPAC Groups 8-10 especially platinum, palladium, rhodium, cobalt, and nickel. Mixtures of metals may be employed.

The finished catalyst compositions can contain the usual binder constituents in amounts which are in the range of from about 10 to about 95 wt %, preferably from about 15 to 50 wt %. The binder is ordinarily an inorganic oxide or mixtures thereof. Both amorphous and crystalline can be employed. Examples of suitable binders are silica, alumina, silica-alumina, clays, zirconia, silica-zirconia and silica-boria. Alumina is a preferred binder material.

For cumene production, the finished catalyst, made of 80 wt % zeolite and 20 wt % alumina binder on a volatile-free basis, preferably has one, and more preferably both, of the following characteristics: (1) an absolute intensity of the modified Y zeolite as measured by X-ray diffraction (XRD) of preferably at least 50, more preferably at least 60; and (2) a framework aluminum of the modified Y zeolite of preferably at least 60%, more preferably at least 70%, of the aluminum of the modified Y zeolite. In one example, the finished catalyst for cumene production has a product of the absolute intensity of the modified Y zeolite as measured by XRD and the % framework aluminum of the aluminum in the modified Y zeolite that is greater than 4200. For ethylbenzene production, the finished catalyst preferably has one, and more preferably both, of the following characteristics: (1) an absolute intensity of the modified Y zeolite as measured by X-ray diffraction (XRD) of preferably at least 65, more preferably at least 75; and (2) a framework aluminum of the modified Y zeolite of preferably at least 50%, more preferably at least 60%, of the aluminum of the modified Y zeolite. In one example, the finished catalyst for cumene production has a product of the absolute intensity of the modified Y zeolite as measured by XRD and the % framework aluminum of the aluminum in the modified Y zeolite that is greater than 4500. As illustrated in FIGS. 1-4 and the examples below, the disclosed catalysts provide increase catalyst activity and, in the case of cumene production, lower NPB formation. In the case of ethylbenzene production from poly-ethylbenzenes (FIG. 5), while internal isomerization of ethyl groups is of little concern and even though an ethyl group is smaller than a propyl group, the diffusion characteristics of the disclosed catalysts appear to be important.

In one embodiment, the process disclosed herein uses a catalyst that is substantially dry. The low pH, ammonium ion exchange is not necessarily followed by a calcination step that drives off substantially all of the water present. It has been found that the performance of the catalyst in the process described herein is improved by removing water. In order to maintain high activity and low NPB formation, it has been found that the water content of the zeolite must be relatively low before it is used in the transalkylation process.

Excess water may reduce the number of active sites and restrict diffusion to them so they do not efficiently catalyze transalkylation. To address this problem, dehydration of the catalyst particles so they contain the desired amount of water may be carried out, prior to start-up, with a drying agent that may be introduced into the transalkylation reaction zone, as the temperature in the reaction zone may be slowly increased to before the aromatic substrate or the transalkylatable aromatic is introduced. During this initial heat-up period, the water content of the zeolite is determined by the equilibrium between the zeolite, the catalyst, the drying agent, and the amount of water in the reaction zone, if any, at temperatures in the reaction zone The zeolitic portion of the catalyst is highly hydrophilic and the level of hydration is controlled by adjusting the rate at which the drying agent passes over the catalyst and the temperature during the dehydration step. The drying agent may be any agent that removes water and does not have a deleterious effect on the catalyst, such as molecular nitrogen, air, or benzene. The temperature during the dehydration step is maintained between about 25 and about 500° C. (~77 to ~932° F.). The water content of the catalyst is calculated by measuring weight loss on ignition (LOI), which is normally determined by calculating the weight loss after heating for about 2 hours at about 900° C. (~1652° F.), and then subtracting the amount of weight loss due to ammonium ion decomposition into ammonia. Since a catalyst containing water in excess of the desired amount, i.e., greater than the equilibrium amount of water the catalyst will contain at any time during process start-up, will lose water once equilibrium is established during start-up, it is not necessary, though it may be desirable, for the dehydration step to be carried out to give the catalyst an amount of water that is equal to or less than the equilibrium amount.

Some desired properties of the catalyst, such as crush strength and ammonium ion concentration, are achieved by controlling the time and temperature conditions at which the extruded catalyst particles are calcined. In some cases, calcination at higher temperatures will leave the required amount of water in the catalyst and thereby make it unnecessary to carry out a separate dehydration step. Thus, "dehydrating" and "dehydration" as used herein not only mean a separate step in which water is removed to the catalyst after calcination but also encompass a calcination step carried out under conditions such that the desired amount of water remains on the catalyst particles.

The dehydration procedure described above is part of the actual process of making the disclosed catalyst at the manufacturing plant. It will be understood, however, that procedures other than that described above can be used to dehydrate the catalyst either in the manufacturing plant at the time the catalyst is made or at some other time at the manufacturing plant or elsewhere. For example, the extruded catalyst particles can be dehydrated in-situ in the transalkylation reactor by passing a water-deficient containing gas, such as dry molecular nitrogen or air, or a dry reactant, such as dry aromatic substrate (e.g., benzene) or dry transalkylatable aromatic (e.g., DIPB or TIPB), over the catalyst at relatively high temperatures until the catalyst contains the desired amount of water. In an in-situ dehydration step, the water-deficient gas or reactant typically contains less than about 30 wt-ppm water, and the contacting is done at a temperature between about 25° C. (~77° F.) to about 500° C. (~932° F). In one example, the catalyst is contacted with flowing dry nitrogen in the gas phase at about 250° C. (~482° F.). The catalyst is contacted with flowing dry benzene in the liquid phase at, for example, about 130° C. (~266° F.) to about 260° C. (~500° F.), about 160° C. (~320° F.) to about 210° C. (~410° F.), about 180° C. (~356° F.) to about 200° C. (~392° F.), or about 150° C. (~302° F.) to about 180° C. (~356° F.). Also, the catalyst particles can be stored at the manufacturing plant or elsewhere so that they are in contact with a surrounding gas until the desired amount of water has been desorbed.

Typically, the LOI of the catalyst that is loaded into the transalkylation reactor is in the range of from about 2 to about 4 wt %. After loading in the reactor, and preferably prior to using the catalyst to promote transalkylation reactions, the catalyst may be subjected to the dehydration step to decrease the water content of the catalyst. The nitrogen content of the catalyst is also preferably minimized.

The disclosed catalyst is useful in the transalkylation of transalkylatable aromatics. The transalkylation process disclosed herein preferably accepts as feed a transalkylatable hydrocarbon in conjunction with an aromatic substrate. The transalkylatable hydrocarbons useful in the transalkylation process are comprised of aromatic compounds which are characterized as constituting an aromatic substrate based molecule with one or more alkylating agent compounds taking the place of one or more hydrogen atoms around the aromatic substrate ring structure. The alkylating agent compounds which may be selected from a group of diverse materials including monoolefins, diolefins, polyolefins, acetylenic hydrocarbons, and also alkylhalides, alcohols, ethers esters, the later including the alkylsulfates, alkylphosphates and various esters of carboxylic acids. The preferred olefin-acting compounds are olefinic hydrocarbons which comprise monoolefins containing one double bond per molecule. Monoolefins which may be utilized as olefin-acting compounds in the disclosed process are either normally gaseous or normally liquid and include ethylene, propylene, 1-butene, 2-butene, isobutylene, and the high molecular weight normally liquid olefins such as the various pentenes, hexenes, heptenes, octenes, and mixtures thereof, and still higher molecular weight liquid olefins, the latter including various olefin oligomers having from about 9 to about 18 carbon atoms per molecule including propylene trimer, propylene tetramer, propylene pentamer, etc. $C_9$ to $C_{18}$ normal olefins may be used as may cycloolefins such as cyclopentene, methylcyclopentene, cyclohexene, methylcyclohexene, etc. may also be utilized, although not necessarily with equivalent results. It is preferred that the monoolefin contains at least 2 and not more than 14 carbon atoms. More specifically, it is preferred that the monoolefin is propylene. The alkylating agent compounds are preferably $C_2$-$C_{14}$ aliphatic hydrocarbons, and more preferably propylene.

The aromatic substrate useful as a portion of the feed to the transalkylation process may be selected from a group of aromatic compounds which include individually and in admixture with benzene and monocyclic alkylsubstituted benzene having the structure:

where R is a hydrocarbon containing 1 to 14 carbon atoms, and n is an integer from 1 to 5. In other words, the aromatic substrate portion of the feedstock may be benzene, benzene containing from 1 to 5 alkyl group substituents, and mixtures thereof. Non-limiting examples of such feedstock compounds include benzene, toluene, xylene, ethylbenzene, mesitylene(1,3,5-trimethylbenzene), cumene, n-propylbenzene, butylbenzene, dodecylbenzene, tetradecylbenzene, and mixtures thereof. It is specifically preferred that the aromatic substrate is benzene.

The disclosed transalkylation process may have a number of purposes. In one, the catalyst of the transalkylation reaction zone is utilized to remove the alkylating agent compounds in excess of one from the ring structure of polyalkylated aromatic compounds and to transfer the alkylating agent compound to an aromatic substrate molecule that has not been previously alkylated, thus increasing the amount of the desired aromatic compounds produced by the process. In a related purpose, the reaction performed in the transalkylation reaction zone involves the removal of all alkylating agent components from a substituted aromatic compound and in doing so, converting the aromatic substrate into benzene.

The feed mixture has a concentration of water and oxygen-containing compounds in the combined feed of preferably less than about 20 wt-ppm, more preferably less than about 10 wt-ppm, and yet more preferably less than about 2 wt-ppm based on the weight of the transalkylatable aromatic and an aromatic substrate passed to the reaction zone. The method by which such low concentrations in the feed mixture are attained is not critical to the process disclosed herein. Usually, one stream containing the transalkylatable aromatic and another stream containing the aromatic substrate are provided, with each stream having a concentration of water and oxygen-containing compounds precursors such that the feed mixture formed by combining the individual streams has the desired concentration. Water and oxygen-containing compounds can be removed from either the individual streams or the feed mixture by conventional methods, such as drying, adsorption, or stripping. Oxygen-containing compounds may be any alcohol, aldehyde, epoxide, ketone, phenol or ether that has a molecular weight or boiling point within the range of molecular weights or boiling points of the hydrocarbons in the feed mixture.

To transalkylate polyalkylaromatics with an aromatic substrate, a feed mixture containing an aromatic substrate and polyalkylated aromatic compounds in mole ratios ranging from about 1:1 to about 50:1 and preferably from about 1:1 to about 10:1 are continuously or intermittently introduced into a transalkylation reaction zone containing the disclosed catalyst at transalkylation conditions including a temperature from about 60 to about 390° C. (~140 to ~734° F.), and especially from about 70 to about 200° C. (~158 to ~392° F.). Pressures which are suitable for use herein preferably are above 1 atmosphere (101.3 kPa(a)) but should not be in excess of about 130 atmospheres (13169 kPa(a)). An especially desirable pressure range is from about 10 to about 40 atmospheres (~1013 to ~4052 kPa(a)). A weight hourly space velocity (WHSV) of from about 0.1 to about 50 hr$^{-1}$, and especially from about 0.5 to about 5 hr$^{-1}$, based upon the polyalkylaromatic feed rate and the total weight of the catalyst on a dry basis, is desirable. While the process disclosed herein may be performed in the vapor phase, it should be noted that the temperature and pressure combination utilized in the transalkylation reaction zone is preferred to be such that the transalkylation reactions take place in essentially the liquid phase. In a liquid phase transalkylation process for producing monoalkylaromatics, the catalyst is continuously washed with reactants, thus preventing buildup of coke precursors on the catalyst. This results in reduced amounts of carbon forming on said catalyst in which case catalyst cycle life is extended as compared to a gas phase transalkylation process in which coke formation and catalyst deactivation is a major problem. Additionally, the selectivity to monoalkylaromatic production, especially cumene production, is higher in the catalytic liquid phase transalkylation reaction herein as compared to catalytic gas phase transalkylation reaction.

Transalkylation conditions for the process disclosed herein include a molar ratio of aromatic ring groups per alkyl group of generally from about 1:1 to about 25:1. The molar ratio may be less than 1:1, and it is believed that the molar ratio may be 0.75:1 or lower. Preferably, the molar ratio of aromatic ring groups per alkyl propyl group (or per propyl group, in cumene production) is below 6:1.

At transalkylation conditions, the catalyst particles typically contain water in an amount preferably below about 4 wt %, more preferably below about 3 wt %, and yet more preferably below about 2 wt %, as measured by Karl Fischer titration, and nitrogen in an amount preferably below about 0.05 wt %, as measured by micro (CHN) (carbon-hydrogen-nitrogen) analysis.

All references herein to the groups of elements of the periodic table are to the IUPAC "New Notation" on the Periodic Table of the Elements in the inside front cover of the book entitled *CRC Handbook of Chemistry and Physics*, ISBN 0-8493-0480-6, CRC Press, Boca Raton, Fla., U.S.A., 80$^{th}$ Edition, 1999-2000.

As used herein, the molar ratio of aromatic ring groups per alkyl group is defined as follows. The numerator of this ratio is the number of moles of aromatic ring groups passing through the reaction zone during a specified period of time. The number of moles of aromatic ring groups is the sum of all aromatic ring groups, regardless of the compound in which the aromatic ring group happens to be. For example, in cumene production one mole of benzene, one mole of cumene, one mole of DIPB, and one mole of TIPB each contribute one mole of aromatic ring group to the sum of aromatic ring groups. In ethylbenzene (EB) production, one mole of benzene, one mole of EB, and one mole of di-ethylbenzene (DEB) each contribute one mole of aromatic ring group to the sum of aromatic ring groups. The denominator of this ratio is the number of moles of alkyl groups that have the same number of carbon atoms as that of the alkyl group on the desired monoalkylated aromatic and which pass through the reaction zone during the same specified period of time. The number of moles of alkyl groups is the sum of all alkyl and alkenyl groups with the same number of carbon atoms as that of the alkyl group on the desired monoalkylated aromatic, regardless of the compound in which the alkyl or alkenyl group happens to be, except that paraffins are not included. Thus, the number of moles of propyl groups is the sum of all iso-propyl, n-propyl, and propenyl groups, regardless of the compound in which the iso-propyl, n-propyl, or propenyl group happens to be, except that paraffins, such as propane, n-butane, isobutane, pentanes, and higher paraffins are excluded from the computation of the number of moles of propyl groups. For example, one mole of propylene, one mole of cumene, and one mole of NPB each contribute one mole of propyl group to the sum of propyl groups, whereas one mole of DIPB contributes two moles of propyl groups and one mole of tri-proplybenzene contributes three moles of propyl groups regardless of the distribution of the three groups between iso-propyl and n-propyl groups One mole of ethylene and one mole of EB each contribute one mole of ethyl groups to the sum of ethyl groups, whereas one mole of DEB contributes two moles of ethyl groups and one mole of tri-ethylbenzene contributes three moles of ethyl groups. Ethane contributes no moles of ethyl groups.

As used herein, WHSV means weight hourly space velocity, which is defined as the weight flow rate per hour divided by the catalyst weight, where the weight flow rate and the catalyst weight are in the same weight units.

As used herein, DIPB conversion is defined as the difference between the moles of DIPB in the feed and the moles of DIPB in the product, divided by the moles of DIPB in the feed, multiplied by 100.

All references herein to surface area are calculated using nitrogen partial pressure p/po data points ranging from about 0.03 to about 0.30 using the BET (Brunauer-Emmett-Teller) model method using nitrogen adsorption technique as described in ASTM D4365-95, Standard Test Method for Determining Micropore Volume and Zeolite Area of a Catalyst, and in the article by S. Brunauer et al, J. Am. Chem. Soc., 60(2), 309-319 (1938).

As referred to herein, the absolute intensity by X-ray powder diffraction (XRD) of a Y zeolite material was measured by computing the normalized sum of the intensities of a few selected XRD peaks of the Y zeolite material and dividing that sum by the normalized sum of the intensities of a few XRD peaks of the alpha-alumina NBS 674a intensity standard, which is the primary standard and which is certified by the National Institute of Standards and Technology (NIST), an agency of the U.S. Department of Commerce. The Y zeolite's absolute intensity is the quotient of the sums multiplied by 100:

$$\text{Absolute Intensity} = \frac{\left(\begin{array}{c}\text{Normalized Intensity of Y}\\ \text{Zeolite Material Peaks}\end{array}\right) \times 100}{\left(\begin{array}{c}\text{Normalized Intensity of}\\ \text{Alpha-Alumina Standard Peaks}\end{array}\right)}$$

The scan parameters of the Y zeolite material and the alpha-alumina standard are shown in Table 1.

TABLE 1

| | Material | |
|---|---|---|
| | Y zeolite | Alpha-alumina standard |
| 2T Ranges | 4-56 | 24.6-26.6, 34.2-36.2, 42.4-44.4 |
| Step Time | 1 sec/step or more depending on zeolite content | 1 sec/step |
| Step Width | 0.02 | 0.01 |
| Peaks | (511, 333), (440), (533), (642), (751, 555) + (660, 822), (664) | (012), (104), (113) |

For purposes of this disclosure, the absolute intensity of a Y zeolite that is mixed with a nonzeolitic binder to give a mixture of Z parts by weight of the Y zeolite and (100–Z) parts by weight of the nonzeolitic binder on a dry basis can be computed from the absolute intensity of the mixture, using the formula, A=C (100/Z), where A is the absolute intensity of the Y zeolite and C is the absolute intensity of the mixture. For example, where the Y zeolite is mixed with $HNO_3$-peptized Pural SB alumina to give a mixture of 80 parts by weight of zeolite and 20 parts by weight $Al_2O_3$ binder on a dry basis, and the measured absolute intensity of the mixture is 60, the absolute intensity of the Y zeolite is computed to be (60)·(100/80) or 75.

As used herein, the unit cell size, which is sometimes referred to as the lattice parameter, means the unit cell size calculated using a method which used profile fitting to find the XRD peak positions of the (642), (822), (555), (840) and (664) peaks of faujasite and the silicon (111) peak to make the correction.

As used herein, the bulk $Si/Al_2$ mole ratio of a zeolite is the silica to alumina ($SiO_2$ to $Al_2O_3$) mole ratio as determined on the basis of the total or overall amount of aluminum and silicon (framework and non-framework) present in the zeolite, and is sometimes referred to herein as the overall silica to alumina ($SiO_2$ to $Al_2O_3$) mole ratio. The bulk $Si/Al_2$ mole ratio is obtained by conventional chemical analysis which includes all forms of aluminum and silicon normally present.

As used herein, the fraction of the aluminum of a zeolite that is framework aluminum is calculated based on bulk composition and the Kerr-Dempsey equation for framework aluminum from the article by G. T. Kerr, A. W. Chester, and D. H. Olson, *Acta Phys. Chem.*, 1978, 24, 169, and the article by G. T. Kerr, *Zeolites*, 1989, 9, 350.

As used herein, dry basis means based on the weight after drying in flowing air at a temperature of about 900° C. (~1652° F.) for about 1 hr.

The following examples are presented for purposes of illustration only and are not intended to limit the scope of this disclosure.

EXAMPLE 1

Comparative

A sample of Y-74 zeolite was slurried in a 15 wt % $NH_4NO_3$ aqueous solution and the solution temperature was brought up to 75° C. (167° F.). Y-74 zeolite is a stabilized sodium Y zeolite with a bulk $Si/Al_2$ ratio of approximately 5.2, a unit cell size of approximately 24.53, and a sodium content of approximately 2.7 wt % calculated as $Na_2O$ on a dry basis. Y-74 zeolite is prepared from a sodium Y zeolite with a bulk $Si/Al_2$ ratio of approximately 4.9, a unit cell size of approximately 24.67, and a sodium content of approximately 9.4 wt % calculated as $Na_2O$ on a dry basis that is ammonium exchanged to remove approximately 75% of the Na and then steam de-aluminated at approximately 600° C. (1112° F.) by generally following steps (1) and (2) of the procedure described in col. 4, line 47 to col. 5, line 2 of U.S. Pat. No. 5,324,877. Y-74 zeolite is produced and was obtained from UOP LLC, Des Plaines, Ill. USA. After 1 hour of contact at 75° C. (167° F.), the slurry was filtered and the filter cake was washed with an excessive amount of warm de-ionized water These $NH_4^+$ ion exchange, filtering, and water wash steps were repeated two more times, and the resulting filter cake had a bulk $Si/Al_2$ ratio of 5.2, a sodium content of 0.13 wt % calculated as $Na_2O$ on a dry basis, a unit cell size of the 24.572 Å and an absolute intensity of 96 as determined X-ray diffraction. The resulting filter cake was dried to an appropriate moisture level, mixed with $HNO_3$-peptized Pural SB alumina to give a mixture of 80 parts by weight of zeolite and 20 parts by weight $Al_2O_3$ binder on a dry basis, and then extruded into 1.59 mm (1/16 in) diameter cylindrical extrudate. The extrudate was dried and calcined at approximately 600° C. (1112° F.) for one hour in flowing air. This catalyst was representative of the existing art. This catalyst had a unit cell size of 24.494 Å, an XRD absolute intensity of 61.1, and 57.2% framework aluminum as a percentage of the aluminum in the modified Y zeolite.

EXAMPLE 2

As synthesized Y-54 zeolite was ammonium exchanged and then treated with ammonium fluorosilicate according to the procedure described in U.S. Pat. No. 4,503,023. Y-54 zeolite is a sodium Y zeolite with a bulk $Si/Al_2$ ratio of approximately 4.9, a unit cell size of 24.67, and a sodium content of 9.4 wt % calculated as $Na_2O$ on a dry basis. Y-54 zeolite is produced and was obtained from UOP LLC, Des Plaines, Ill. USA. The resulting Y zeolite, which had a bulk $Si/Al_2$ molar ratio of about 6.5, was steamed at about 600° C. (1112° F.) with 100% steam for 1 hour, and then ammonium exchanged. The resulting filter cake was dried to an appropriate moisture level, mixed with $HNO_3$-peptized Pural SB alumina to give a mixture of 80 parts by weight of zeolite and 20 parts by weight $Al_2O_3$ binder on a dry basis, and then extruded into 1.59 mm (1/16 in) diameter cylindrical extrudate. The extrudate was dried and calcined at approximately 600° C. (1112° F.) for one hour in flowing air. The resulting catalyst had a unit cell size of 24.426 Å, an absolute XRD intensity of 81.6, and 63.2% framework aluminum as a percentage of the aluminum in the modified Y zeolite.

EXAMPLE 3

As synthesized Y-54 zeolite was ammonium exchanged and then treated with ammonium fluorosilicate according to the procedure described in U.S. Pat. No. 4,503,023. The resulting Y zeolite, which had a bulk $Si/Al_2$ molar ratio of about 9.0 and was referred to as LZ-210(9), was steamed at about 600° C. (1112° F.) with 100% steam for 1 hour. A slurry made up of 228 g of the steamed LZ-210(9) and 672 g of $H_2O$ was first prepared. A $NH_4NO_3$ solution made up of 212 g of $H_2O$ and 667 g of 50 wt % $(NH_4)NO_3$ was then added to the steamed LZ-210(9) slurry. The resulting mixture was then raised to 85° C. (185° F.) and then mixed for 15 minutes. To this mixture, 5.7 g of 66 wt % $HNO_3$ were added, and the resulting mixture was maintained at 85° C. (185° F.) with continuous agitation for 60 minutes. At the end of acid extraction, the mixture was filtered and the cake was washed with 1000 ml of $H_2O$, and then dried at 100° C. (212° F.) overnight. In the second part, 200 g of dry cake was added to a solution made up of 667 g of 50 wt % $(NH_4)NO_3$ and 650 g of $H_2O$, to which 20 g of 66 wt % $HNO_3$ was added. The resulting slurry was mixed for 60 minutes. Thereafter, the mixture was filtered, washed with 1000 ml of $H_2O$ and the filter cake was oven dried at 100° C. (212° F.) overnight. The resulting zeolite had a 10.82 bulk Si/Ah ratio and 0.026 wt % $Na_2O$. The zeolite powder was mixed with $HNO_3$-peptized Pural SB alumina to give a mixture of 80 parts by weight of zeolite and 20 parts by weight $Al_2O_3$ binder on a dry basis, moisture adjusted to give proper dough texture and then extruded into 1.59 mm (1/16 in) diameter cylindrical extrudate. The extrudate was dried and calcined at approximately 600° C. (1112° F.) for one hour in flowing air. The resulting catalyst had a unit cell size of 24.430 Å, an absolute XRD intensity of 78.4, 77.8% framework aluminum and a BET surface area of 661 $m^2/g$.

EXAMPLE 4

As synthesized Y-54 zeolite was ammonium exchanged and then treated with ammonium fluorosilicate according to the procedure described in U.S. Pat. No. 4,503,023. The resulting Y zeolite, which had a bulk $Si/Al_2$ molar ratio of about 9.0 and was referred to as LZ-210(9), was steamed at about 600° C. (1112° F.) with 100% steam for 1 hour. An amount of 256 g of the steamed LZ-210(9) was added to 1140 g of 22 wt % $NH_4NO_3$. To the zeolite slurry, 368 g of 17 wt % $HNO_3$ was slowly added over a period of 30 minutes. The slurry was then heated up to 80° C. (176° F.) and held at 80° C. (176° F.) for 90 minutes. At the end of acid extraction, the slurry was quenched with 1246 g of $H_2O$, filtered, washed with 1140 g of a 22 wt % $NH_4NO_3$, washed with 1000 ml of $H_2O$ and oven dried at 100° C. (212° F.) overnight. The resulting zeolite had a bulk 14.38 $Si/Al_2$ ratio and 0.047 wt % $Na_2O$. The resulting zeolite powder was mixed with $HNO_3$-peptized Pural SB alumina to give a mixture of 80 parts by weight of zeolite and 20 parts by weight $Al_2O_3$ binder on a dry basis, moisture adjusted to give proper dough texture and then extruded into 1.59 mm (1/16 in) diameter cylindrical extrudate. The extrudate was dried and calcined at approximately 600° C. (1112° F.) for one hour in flowing air. The resulting catalyst had a unit cell size of 24.393 Å, an absolute XRD intensity of 79.6, 81.8% framework aluminum, and a BET surface area of 749 $m^2/g$.

EXAMPLE 5

As synthesized Y-54 zeolite was ammonium exchanged and then treated with ammonium fluorosilicate according to the procedure described in U.S. Pat. No. 4,503,023. The resulting Y zeolite, which had a bulk $Si/Al_2$ molar ratio of about 12 and was referred to as LZ-210(12), was steamed at about 600° C. (1112° F.) with 100% steam for 1 hour. A slurry made up of 231 g of the steamed LZ-210(12) and 668 g of $H_2O$ was first prepared. A $NH_4NO_3$ solution made up of 212 g of $H_2O$ and 667 g of 50 wt % $(NH_4)NO_3$ was then added to the steamed LZ-210(12) slurry. The resulting mixture was then raised to 85° C. (185° F.) and then mixed for 15 minutes. To this mixture, 33.4 g of 66 wt % $HNO_3$ were added, and the resulting mixture was maintained at 85° C. (185° F.) with continuous agitation for 60 minutes. At the end of acid extraction, the mixture was filtered and the cake was washed with 1000 ml of $H_2O$, and then dried at 100° C. (212° F.) overnight. In the second part, 200 g of dry cake was added to a solution made up of 667 g of 50% $(NH_4)NO_3$ and 650 g of $H_2O$, to which 10 g of 66 wt % $HNO_3$ were added. The resulting slurry was mixed for 60 minutes. Thereafter, the mixture was filtered, washed with 1000 ml of $H_2O$ and the filter cake was oven dried at 100° C. (212° F.) overnight. The resulting zeolite had a 17.24 bulk $Si/Al_2$ ratio and 0.01 wt % $Na_2O$. The resulting zeolite powder was mixed with $HNO_3$-peptized Pural SB alumina to give a mixture of 80 parts by weight of zeolite and 20 parts by weight $Al_2O_3$ binder on a dry basis, moisture adjusted to give proper dough texture and then extruded into 1.59 mm (1/16 in) diameter cylindrical extrudate. The extrudate was dried and calcined at approximately 600° C. (1112° F.) for one hour in flowing air. The resulting catalyst had a unit cell size of 24.391 Å, an absolute XRD intensity of 81.2, 94.9% framework aluminum and a BET surface area of 677 $m^2/g$.

EXAMPLE 6

An amount of 250 g of the LZ-210(12) from Example 5 (before steaming) was added to a $NH_4NO_3$ solution made up of 500 g of 50% $NH_4NO_3$ and 625 g of $H_2O$. The slurry was heated up to 95° C. (203° F.) and hold at temperature for 2 hours. The slurry was then filtered and water washed. The cake was then $NH_4NO_3$ exchanged and water washed a second time following the same procedure. The filter cake was oven dried at 100° C. (212° F.) overnight. The resulting zeolite had a 12.62 bulk $Si/Al_2$ ratio and 0.05 wt % $Na_2O$. The dried zeolite was mixed with $HNO_3$-peptized Pural SB alumina to give a mixture of 80 parts by weight of zeolite and 20 parts by weight $Al_2O_3$ binder on a dry basis, moisture adjusted to give appropriate dough texture and then extruded into 1.59 mm (1/16 in) diameter cylindrical extrudate. The extrudate was dried and calcined at approximately 600° C. (1112° F.) for one hour in flowing air. The resulting catalyst had a unit cell size of 24.431 Å, an absolute XRD intensity of 77.3, 89.2% framework aluminum and a BET surface area of 660 $m^2/g$.

Table 2 summarizes the properties of the catalysts prepared in Examples 1-6.

TABLE 3

| Component | Concentration, wt % |
|---|---|
| Benzene | 63.832 |
| Nonaromatics | 0.038 |
| Toluene | 0.002 |
| Ethylbenzene | 0.000 |
| Cumene | 0.880 |
| NPB | 0.002 |
| Butylbenzene | 0.071 |
| Pentylbenzene | 0.021 |
| m-DIPB | 20.776 |
| o-DIPB | 0.520 |
| p-DIPB | 13.472 |
| Hexylbenzene | 0.308 |
| 1,3,5-TIPB | 0.029 |
| 1,2,4-TIPB | 0.012 |
| Tetra-isopropylbenzene | 0.003 |
| Nonylbenzene | 0.004 |
| Unknowns | 0.030 |
| Total | 100.000 |

TABLE 2

| | Example | | | | | | |
|---|---|---|---|---|---|---|---|
| | 1 | 2 | 3 | 4 | 5 | 6 | 8 |
| Type of Example | Comparative | Example | Example | Example | Example | Example | Example |
| Figures w/Run Data | 1-4 | None | None | 1-4 | 1-2 | 1-2 | 1-2 |
| Y zeolite bulk $Si/Al_2$ ratio, molar | 5.20 | 8.61 | 10.82 | 14.38 | 17.24 | 12.62 | 12.62 |
| Y zeolite unit cell size, Å | 24.494 | 24.426 | 24.430 | 24.393 | 24.391 | 24.431 | 24.439 |
| Catalyst XRD absolute intensity | 61.1 | 81.6 | 78.4 | 79.6 | 81.2 | 77.3 | 72.5 |
| Y zeolite XRD absolute intensity | 76.4 | 102 | 98 | 99.5 | 101.5 | 96.6 | 90.6 |
| Y zeolite frame work aluminum, atomic % of total aluminum | 57.2 | 63.2 | 77.8 | 81.8 | 94.9 | 89.2 | 92.6 |
| Catalyst BET surface area, $m^2/g$ | — | — | 661 | 749 | 677 | 660 | 660 |

EXAMPLE 7

The catalysts prepared in the Examples 1 and 4-6 were tested for transalkylation performance using a feed containing benzene and polyalkylated benzenes. The feed was prepared by blending polyalkylated benzenes obtained from a commercial transalkylation unit with benzene. The feed composition as measured by gas chromatography is summarized in Table 3. The test was done in a fixed bed reactor in a once-through mode under conditions of 3447 kPa(g) (500 psi(g)) reactor pressure, a molar ratio of aromatic ring groups per propyl group of 2.3, and a 0.8 $hr^{-1}$ DIPB WHSV over a range of reaction temperatures. The reactor was allowed to achieve essentially steady-state conditions at each reaction temperature, and the product was sampled for analysis. Essentially no catalyst deactivation occurred during the test. Prior to introducing the feed, each catalyst was subjected to a drying procedure by contacting with a flowing nitrogen stream containing less than 10 wt-ppm water at 250° C. (482° F.) for 6 hours.

Figure 1:
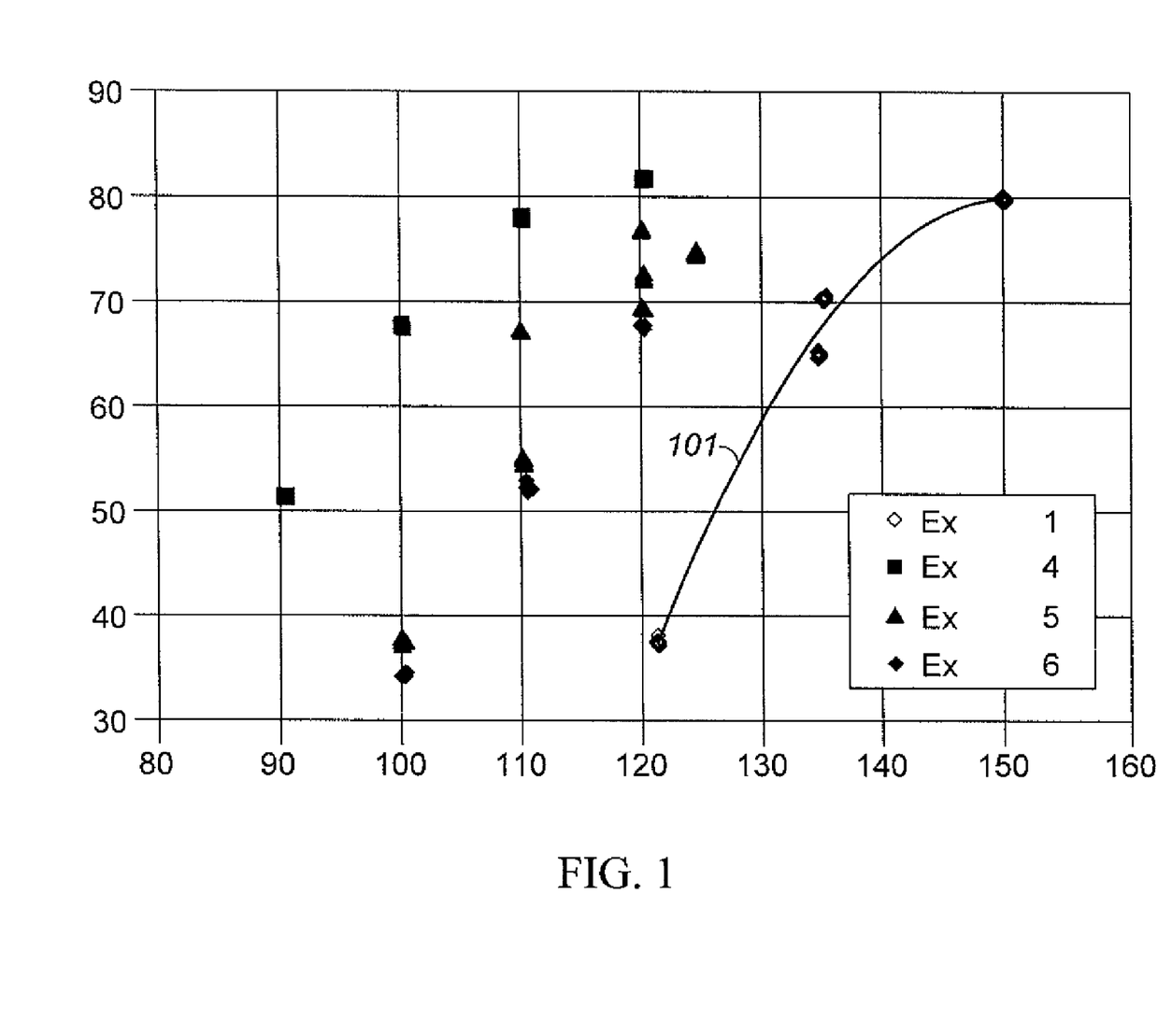
FIG. 1 illustrates, graphically, DIPB conversion (y-axis, %) versus temperature (x-axis, ° C.) for catalysts prepared in accordance with Examples 4-6 of this disclosure against Comparative Example 1.
Figure 2:
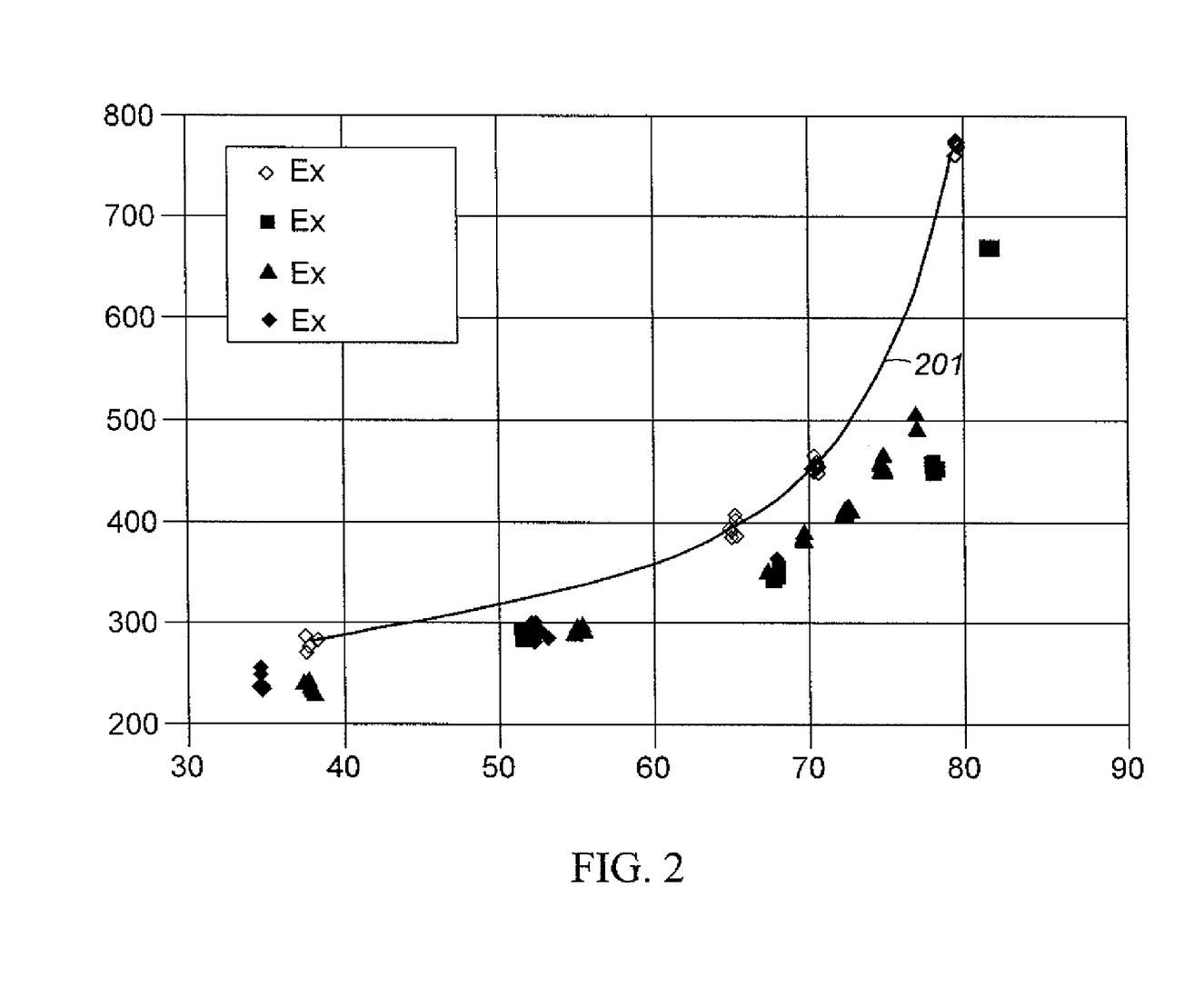
FIG. 2 illustrates, graphically, the ratio of NPB to cumene (y-axis, wt-ppm) in the product versus DIPB conversion (x-axis, %) for the catalysts of Examples 4-6 of this disclosure and against Comparative Example 1.

FIGS. 1 and 2 show the test results for the catalysts prepared in Examples 1 and 4-6. In FIG. 1, the catalysts prepared in Examples 4-6 show higher activities (i.e., higher DIPB conversion at a given temperature) as compared to the curve 101 for Example 1. In FIG. 2, the catalysts prepared in Examples 4-6 also exhibit better product purities (i.e., lower NPB/cumene at a given DIPB conversion) than the curve 201 for the catalyst prepared in Example 1. Referring to FIGS. 1 and 2, the data for Example 6 indicates that the steaming and acid extraction steps are not required in the catalyst preparation, since good performance can be achieved even when both are omitted. Still referring to FIGS. 1 and 2, the data for Example 4 indicates that superior activity and comparable product purity can be achieved using a single-step post-steaming acid extraction, instead of the two-step acid extraction of Example 5, despite the acid extraction conditions being more severe.

EXAMPLE 8

A sample of the catalyst prepared in Example 6 was tested in the manner described in Example 7, as described previously. After testing, the spent catalyst was placed in a ceramic dish, which was placed in a muffle furnace. While flowing air was passed through the muffle furnace, the furnace temperature was raised from 70° C. (158° F.) to 550° C. (1022° F.) at a rate of 1° C. (1.8° F.) per minute, held at 550° C. (1022° F.) for 6 hours, and then cooled to 110° C. (230° F.). The regenerated catalyst had a unit cell size of 24.439 Å, an absolute XRD intensity of 72.5, 92.6% framework aluminum and a BET surface area of 660 m²/g. Table 2 summarizes the properties of the regenerated catalyst. Following regeneration, the catalyst was again tested in the manner described in Example 7. The catalysts before and after regeneration had similar activities (i.e., DIPB conversion at a given temperature) and product purities (i.e., NPB/cumene at a given DIPB conversion) and therefore indicate good catalyst regenerability.

EXAMPLE 9

A sample of the catalyst prepared in Example 4 was tested in the manner described in Example 7, as described previously. After testing, the spent catalyst was regenerated in the manner described in Example 8. Following regeneration, the catalyst was again tested in the manner described in Example 7.

Figure 3:
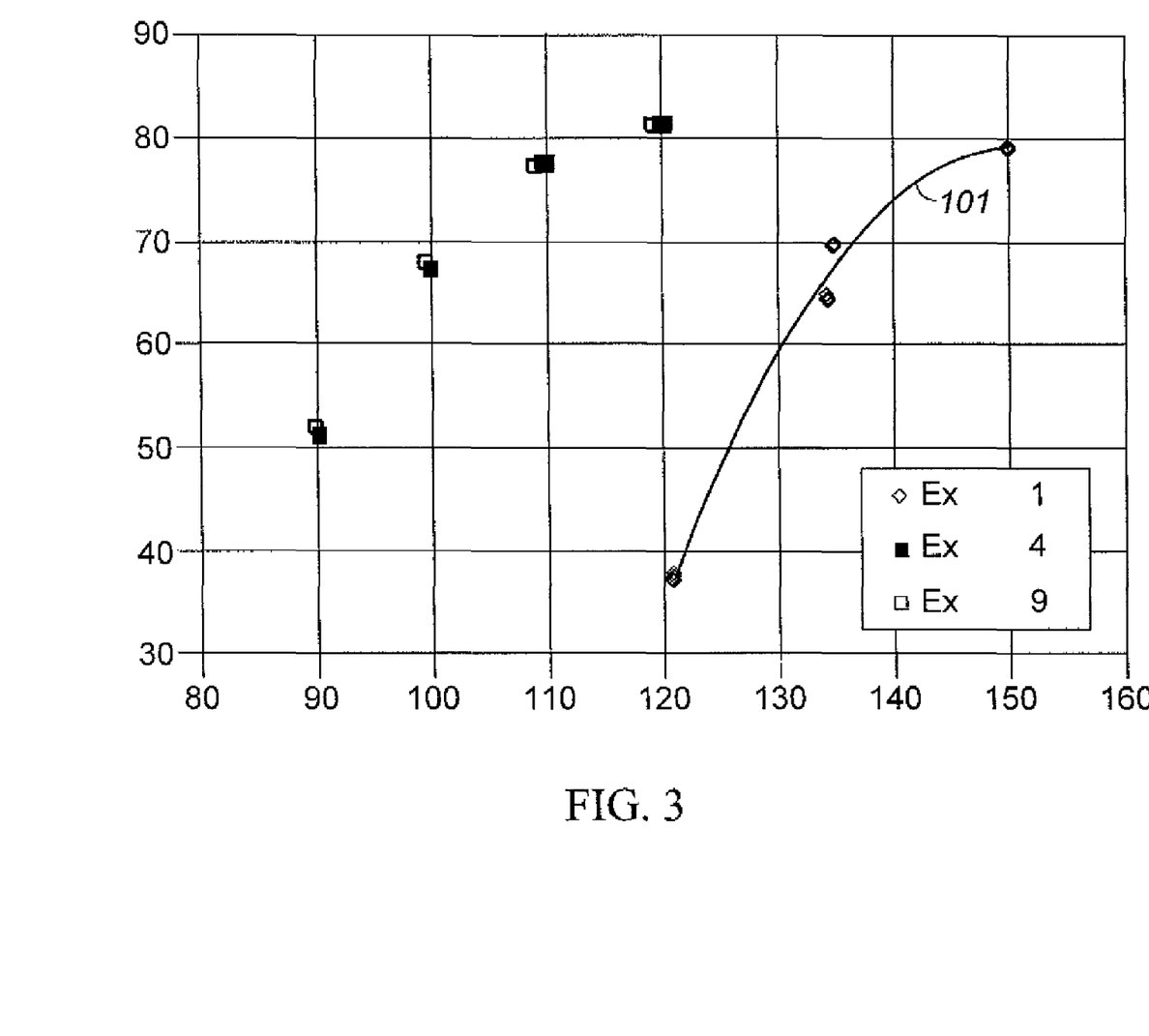
FIG. 3 illustrates, graphically, DIPB conversion (y-axis, %) versus temperature (x-axis, ° C.) for the catalyst of Example 4 before regeneration and after regeneration (Example 9) and against Comparative Example 1.
Figure 4:
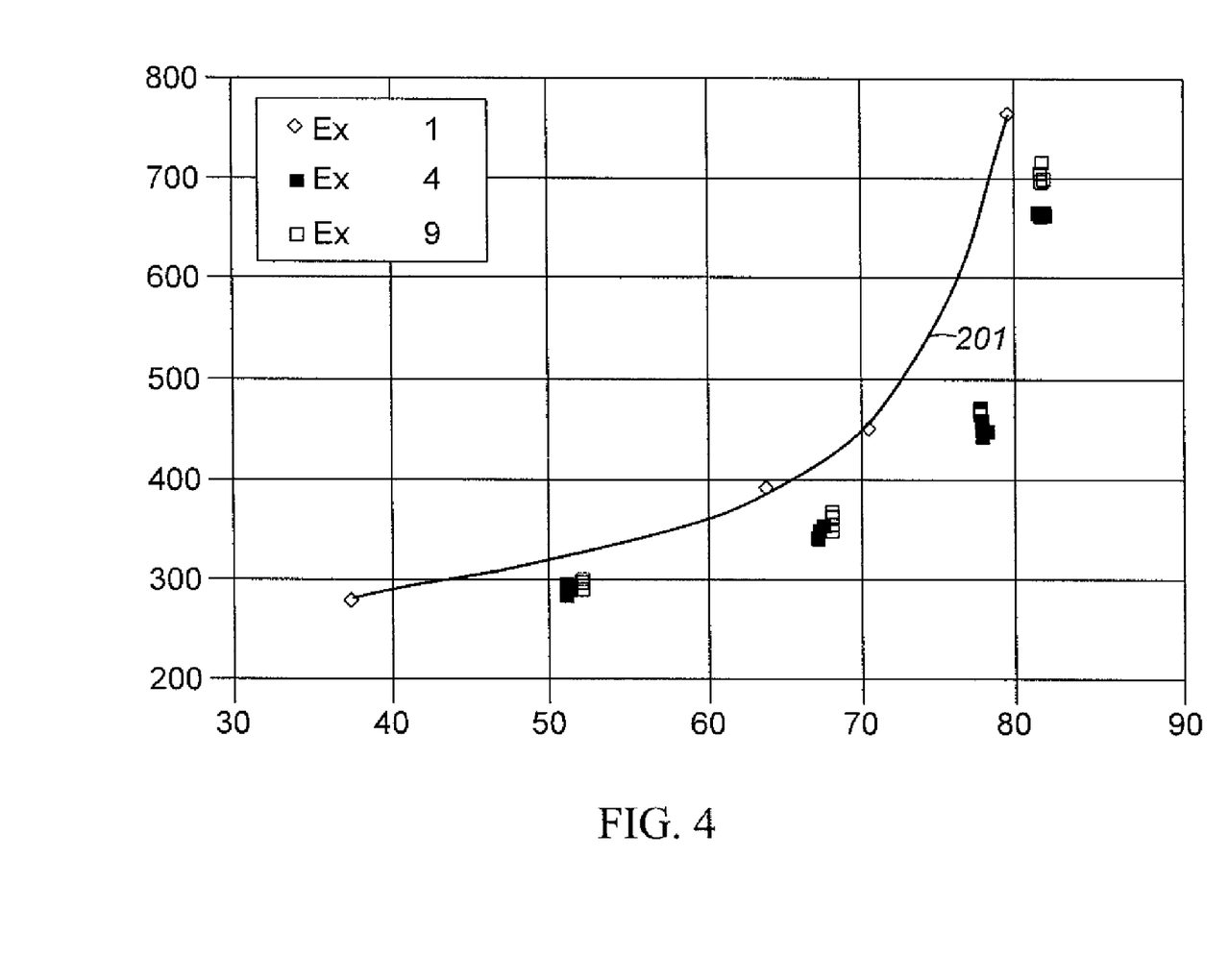
FIG. 4 illustrates, graphically, the ratio of NPB to cumene (y-axis, wt-ppm) in the product versus DIPB conversion (x-axis, %) for the catalyst of Example 4 before regeneration and after regeneration (Example 9) and against Comparative Example 1.

FIGS. 3 and 4 graphically illustrate the test results for the catalysts before regeneration (labeled "Example 4") and after regeneration (labeled "Example 9"). The results indicate that the catalysts before and after regeneration had similar activities (i.e., DIPB conversion at a given temperature) and product purities (i.e., NPB/cumene at a given DIPB conversion) that were both better than the curves 101, 201 of FIGS. 3, 4 respectively for the Example 1 catalyst, and therefore indicate good catalyst regenerability.

These examples show the benefits of high activity and product purity in transalkylating poly-alkylates to cumene attributed to catalysts prepared by the process disclosed herein.

What is claimed is:

1. A process for producing a modified Y zeolite, comprising:
   a) treating a Y zeolite with an aqueous solution of a fluorosilicate salt to give a first LZ-210 zeolite having a first bulk $Si/Al_2$ molar ratio and a first unit cell size;
   b) hydrothermally steaming the first LZ-210 zeolite at a temperature of from about 550° C. to about 850° C. to produce a second LZ-210 zeolite having a bulk $Si/Al_2$ molar ratio about the same as the first bulk $Si/Al_2$ molar ratio and having second unit cell size less than the first unit cell size,
   c) contacting the second LZ-210 zeolite, with a sufficient amount of an aqueous solution of ammonium ions having a pH of less than about 4 for a sufficient time to exchange at least some of the sodium cations in the second LZ-210 zeolite for ammonium and hydrogen ions; and
   d) producing a modified LZ-210 zeolite having a second bulk $Si/Al_2$ molar ratio greater than the first bulk $Si/Al_2$ ratio and ranging from about 6.5 to about 27, wherein 63% to 95% of aluminum in the modified LZ-210 zeolite is framework aluminum.

2. The process of claim 1 wherein the aqueous solution used in part (c) comprises an ion selected from the group consisting of nitrate and sulfate ion.

3. The process of claim 1 wherein the aqueous solution used in part (c) is formed by mixing ammonium nitrate, nitric acid and water.

4. The process of claim 1 wherein the aqueous solution used in part (c) is formed by mixing ammonium sulfate, sulfuric acid and water.

5. The process of claim 1 further comprising the following step prior to treating the Y zeolite with the fluorosilicate salt:
   ammonium ion-exchanging sodium in the Y zeolite to reduce the sodium content thereof to less than about 3 wt % $Na_2O$ based on the weight of the Y zeolite on a water-free basis.

6. The process of claim 1 wherein part (a) further comprises the following step after treating the Y zeolite with the fluorosilicate salt:
   ammonium ion-exchanging sodium in the first LZ-210 zeolite to further lower the sodium content thereof to less than about 3 wt % $Na_2O$ based on the weight of the first LZ-210 zeolite on a water-free basis.

7. The process of claim 1 wherein part (c) further comprises:
   contacting the second LZ-210 zeolite with a first aqueous solution of ammonium ions having a pH of less than 4 to form the first mixture, filtering the first mixture to recover a filter cake, and optionally contacting the filter cake with a second solution of ammonium ions having a pH of less than 4.

8. The process of claim 1 wherein the catalyst is contacted with a dehydration agent having a concentration of water less than 30 wt-ppm and the dehydration agent has a temperature during contact ranging from about 25° C. to about 500° C.

9. The process of claim 1 wherein the hydrothermal steaming is carried out at a temperature ranging from about 600° C. to about 725° C.

10. The process of claim 1 wherein the modified LZ-210 zeolite has a third unit cell size in the range of from about 24.34 Å to about 24.58 Å, an absolute XRD intensity of 50 or higher and the third bulk $Si/Al_2$ molar ratio ranges from about 6.5 to about 27.

11. The process of claim 1 wherein modified LZ-210 zeolite has an absolute intensity as measured by X-ray diffraction of at least 50.

12. The process of claim 1 wherein the catalyst has a loss on ignition (LOI) at 900° C. of less than 3.5 wt %.

13. The process of claim 1 wherein the catalyst has a water content by Karl-Fischer titration of less than 3.5 wt %.

14. The process of claim 1 further comprising:
   a) providing a metal hydrogenation component; and
   b) incorporating less than 0.2 wt % of the metal hydrogenation component into the modified LZ-210 zeolite whereby the modified LZ-210 zeolite has less than 0.2 wt % of the metal hydrogenation component.

15. The process of claim 1 wherein the modified LZ-210 catalyst is devoid of a metal hydrogenation component.

16. The process of claim 1 further characterized in that after part (c) the modified LZ-210 zeolite is contacted with a drying agent having a concentration of water of less than 30 wt-ppm and at a temperature ranging from about 25° C. to about 500° C.

17. A process for producing a modified LZ-210 zeolite having less than 0.2 wt % of a metal hydrogenation component comprising:
   a) treating a Y zeolite with an aqueous solution of a fluorosilicate salt to give a first LZ-210 zeolite with a first bulk $Si/Al_2$ molar ratio of 6.5 or higher;
   b) ammonium ion exchanging the first LZ-210 zeolite to provide the first LZ-210 zeolite with a first unit cell size and a reduced $Na_2O$ wt % of 1 wt % or lower while at least substantially maintaining the first bulk $Si/Al_2$ molar ratio;

c) hydrothermal steaming the first LZ-210 zeolite of part (b) or part (a) at a temperature ranging from about 550° C. to about 850° C. to produce a second LZ-210 zeolite having the first bulk $Si/Al_2$ molar ratio and having a second unit cell size less than the first unit cell size;

d) contacting the second LZ-210 zeolite with a sufficient amount of an aqueous solution of ammonium ions having a pH of less than about 4.0 for a sufficient time to exchange at least some of the sodium cations in the second LZ-210 zeolite for ammonium ions;

e) producing the modified LZ-210 zeolite having a second bulk $Si/Al_2$ molar ratio greater than the first bulk $Si/Al_2$ molar ratio and ranging from about 6.5 to about 27;

f) providing a metal hydrogenation component; and g) incorporating less than 0.2 wt % of the metal hydrogenation component into the modified LZ-210 zeolite;

wherein at least 63% to 95% of the aluminum of the modified LZ-210 zeolite is framework aluminum, the modified LZ-210 zeolite has less than 0.2 wt % of a metal hydrogenation component, and the modified LZ-210 zeolite has an absolute intensity as measured by X-ray diffraction of at least 80.

18. A process for producing a modified LZ-210 zeolite, comprising:

a) treating a Y zeolite with an aqueous solution of a fluorosilicate salt to give a first LZ-210 zeolite having a first bulk $Si/Al_2$ molar ratio and a first unit cell size;

b) hydrothermally steaming the first LZ-210 zeolite at a temperature of from about 550° C. to about 850° C. to produce a second LZ-210 zeolite having a bulk $Si/Al_2$ molar ratio about the same as the first bulk $Si/Al_2$ molar ratio and having second unit cell size less than the first unit cell size, c) contacting the second LZ-210 zeolite with a sufficient amount of an aqueous solution of ammonium ions having a pH of less than about 4 to make an acidified zeolite slurry;

d) heating the acidified zeolite slurry to a temperature from about 80° C. to about 85° C. for a time from about 1 hour to about 1.5 hours to exchange at least some of the sodium cations in the acidified zeolite slurry for ammonium ions and to remove at least some of the aluminum in the acidified zeolite slurry; and d) producing from the acidified zeolite slurry a modified LZ-210 zeolite having a second bulk $Si/Al_2$ molar ratio greater than the first bulk $Si/Al_2$ ratio and ranging from about 6.5 to about 27, wherein 63% to 95% of aluminum in the modified LZ-210 zeolite is framework aluminum.

19. A process for producing a modified LZ-210 zeolite having less than 0.2 wt % of a metal hydrogenation component comprising:

a) treating a Y zeolite with an aqueous solution of a fluorosilicate salt to give a first LZ-210 zeolite with a first bulk $Si/Al_2$ molar ratio of 6.5 or higher;

b) ammonium ion exchanging the first LZ-210 zeolite to provide the first LZ-210 zeolite with a first unit cell size and a reduced $Na_2O$ wt % of 1 wt % or lower while at least substantially maintaining the first bulk $Si/Al_2$ molar ratio;

c) hydrothermal steaming the first LZ-210 zeolite of part (b) or part (a) at a temperature ranging from about 550° C. to about 850° C. to produce a second LZ210 zeolite having the first bulk $Si/Al_2$ molar ratio and having a second unit cell size less than the first unit cell size;

d) contacting the second LZ-210 zeolite with a sufficient amount of an aqueous solution of ammonium ions having a pH of less than about 4 to make an acidified zeolite slurry;

e) heating the acidified zeolite slurry to a temperature from about 80° C. to about 85° C. for a time from about 1 hour to about 1.5 hours to exchange at least some of the sodium cations in the acidified zeolite slurry for ammonium ions and to remove at least some of the aluminum in the acidified zeolite slurry; and f) producing from the acidified zeolite slurry a modified LZ-210 zeolite having, a second bulk $Si/Al_2$ molar ratio greater than the first bulk $Si/Al_2$ ratio and ranging from about 6.5 to about 27, g) providing a metal hydrogenation component; and h) incorporating less than 0.2 wt % of the, metal hydrogenation component into the modified LZ-210 zeolite;

wherein at least 63% to 95% of the aluminum of the modified LZ-210 zeolite is framework aluminum, the modified LZ-210 zeolite has less than 0.2 wt % of a metal hydrogenation component, and the modified LZ-210 zeolite has an absolute intensity as measured by X-ray diffraction of at least 80.

20. The method of claim 18 further comprising the steps of:

a) mixing about 80 parts by weight of modified LZ-210 zeolite on a dry basis with about 20 parts by weight of $Al_2O_3$ on a dry basis to make a mixture;

b) extruding the mixture to make at least one extrudate object; and c) calcining at least one extrudate object at about 600° C. for about 1 hour.

21. The method of claim 19 further comprising the steps of:

a) mixing about 80 parts by weight of modified LZ-210 zeolite on a dry basis with about 20 parts by weight of $Al_2O_3$ on a dry basis to make a mixture;

b) extruding the mixture to make at least one extrudate object; and c) calcining at least one extrudate object at about 600° C. for about 1 hour.

22. The process of claim 6 wherein the modified LZ-210 zeolite is composited with a binder prior to being used at transalkylation conditions.

* * * * *